United States Patent [19]

Deardorff

[11] Patent Number: 4,506,091

[45] Date of Patent: Mar. 19, 1985

[54] REMOVAL OF CATALYST RESIDUES FROM POLYESTERS

[76] Inventor: Donald L. Deardorff, 43 Gould Pl., East Greenwich, R.I. 02818

[21] Appl. No.: 528,411

[22] Filed: Sep. 1, 1983

Related U.S. Application Data

[63] Continuation-in-part of Ser. No. 318,847, Nov. 6, 1981, abandoned.

[51] Int. Cl.$^3$ .................. C07C 67/48; C07C 67/08
[52] U.S. Cl. ............................ 560/99; 203/18; 203/19; 203/38; 203/53; 260/410.9 R; 502/171; 560/1; 560/78; 560/79; 560/103; 560/89; 560/94; 560/106; 560/107; 560/108; 560/121; 560/122; 560/123; 560/124; 560/191; 560/193; 560/194; 560/204; 560/265; 560/218
[58] Field of Search .............. 560/1, 78, 99, 79, 103, 560/106, 107, 89, 94, 108, 121, 122, 123, 124, 191, 193, 194, 204, 265, 218; 203/18, 19, 38, 53; 260/410.9 R; 502/171

[56] References Cited

U.S. PATENT DOCUMENTS

| | | | |
|---|---|---|---|
| 3,056,818 | 10/1962 | Werber | 560/99 X |
| 4,216,337 | 8/1980 | Baba et al. | 560/78 |
| 4,284,793 | 8/1981 | Sagara et al. | 560/78 |

FOREIGN PATENT DOCUMENTS 1058242  2/1967  United Kingdom .

Primary Examiner—Natalie Trousof
Assistant Examiner—Vera C. Clarke
Attorney, Agent, or Firm—Barlow & Barlow

[57] ABSTRACT

A process for preparing esters which comprises reacting a polycarboxylic acid with an excess of alcohol and in the presence of an organotitanate catalyst, treating the crude mixture with a suitable chelate compound, removing the unreacted alcohol and hydrolyzing the treated titanium catalyst residues with steam, and recovering the purified ester by filtration.

7 Claims, No Drawings

REMOVAL OF CATALYST RESIDUES FROM POLYESTERS

CROSS-REFERENCE TO RELATED APPLICATIONS

This application is a continuation-in-part of my prior application Ser. No. 318,847, filed Nov. 6, 1981, now abandoned.

BACKGROUND OF THE INVENTION

Esters derived from carboxylic acids or anhydrides and aliphatic alcohols comprise a large and broadly used class of compounds. Esters of phthalic anhydride, for example, are produced in quantities or more than 1.5 billion pounds per year. Of this group, di-2-ethylhexyl phthalate (DEHP) is the most commonly used member, and is produced in excess of 500 million pounds per year. The largest single use of DEHP, and of several other members of the group, is as a plasticizer for polyvinyl chloride resins. They are also used broadly as solvents, lubricants, functional fluids, additives and the like. A variety of other acids, for example, adipic acid, azelaic acid, terephthalic acid, trimellitic anhydride, benzoic acid and aliphatic acids of both natural and synthetic derivation, are extensively used in ester production. These acids are reacted with aliphatic alcohols containing 4 to 13 carbon atoms in the alkyl chain and 1 to 4 hydroxyl groups, to produce esters having an extremely broad range of properties and applications.

Large scale synthesis of esters began early in the 20th century and grew rapidly, along with related industries, to satisfy needs of plasticization, lubrication, hydraulics and the like. Along with this growth came a need for improved methods of manufacture. In most instances practical synthesis of esters requires catalyzed reactions of the carboxylic acid or anhydride with an excess of alcohols at elevated temperatures. Earlier commercial synthesis procedures usually used strong acids, as for example, sulfuric acid, p-toluene sulfonic acid, or phosphoric acid as catalysts. This type of reaction is carried out at temperatures of 130 to 160 degrees C. Conversions of carboxylic acid to ester are generally 95 to 98 percent complete and reaction mixtures are refined by washing with aqueous caustic to remove residual acids and to help improve color. Excess alcohol is removed by vacuum and steam distillations. Conversion of raw materials to ester is reduced both by acid catalyzed decompositions reactions and, to a greater extent, by losses in washing and filtering procedures.

A significant improvement in commercial esterification procedures was realized with the introduction and use of organometallic compounds as catalysts. These generally require higher temperatures than acid catalysts, typically from 190° to 230° C., but can provide a higher yield of esters due to less tendency for decomposition reactions as well as permitting higher conversions; giving 99.9 percent or more of conversion of acid to ester, compared with 98 to 99 percent by previous acid catalyzed methods. The most successful and widely used of the organometallic catalysts are tetraalkyl titanate esters as described in Werber in U.S. Pat. No. 3,056,818. While other improvements in ester manufacture have been made, particularly in raw material quality and reactor design, washing procedures still are required in commercial esterification processes in order to provide high purity, commercial grades of DEHP and other esters. Such washing is required in order that the titanium catalysts residues may be sufficiently hydrolyzed to avoid (1) increase of acidity during steam distillation, (2) decrease of filtration rate due to coating of filter surfaces with gelatinous catalyst residues, and (3) cloudiness appearing in products after filtration due to imcomplete removal of titanium residues.

This invention provides a new and novel means of removing these titanium catalyst residues and providing high purity esters without the necessity of aqueous washing methods.

SUMMARY OF THE INVENTION

In accordance with this invention, there is provided a novel and improved method for refining of esters manufactured by means of organotitanate catalysis, wherein the crude reaction product may be refined to give high quallity products without the necessity of washing procedures, which are normally necessary with ester production processes using soluble organometallic catalysts. The basis of the present invention is the treatment of the residue esterification product with compounds which have the ability to react with residual catalyst species to produce an intermediate complex which is more easily and efficiently hydrolyzed and removable by standard procedures of steam distillation and filtration than untreated titanate catalyst residues.

Thus, in the present invention, carboxylic acids or their anhydrides are reacted with an excess of aliphatic alcohols at a suitable elevated temperature, generally from 190° to 230° C., in the presence of an organotitanate catalyst, and in a manner suitable to yield a reaction product in which greater than 99.95 weight percent of the initial acids are converted into recoverable ester products.

Suitable reaction conditions for such a process are well known to one skilled in the art, similar procedures being practiced broadly since before 1960 in the manner of Werber (U.S. Pat. No. 3,056,818). Such conditions are described herein and used in examples illustrating the utility of this invention. The reaction products from such a process, comprised essentially of product ester, excess alcohol and catalyst residues are, in the manner of this invention, refined by (a) treating with a suitable chelating agent, (b) removing excess alcohol and at the same time hydrolyzing titanate catalyst residue complexes by means of steam distillation, and (c) filtering insoluble catalyst residues from the purified ester.

Chelating agents and compounds suitable to use in treating of the catalyst residues in this invention are selected from the group listed below and may be used in quantities of 0.5 to 5 mole equivalents of titanium present in the original reaction mixture. Compounds suitable as chelating or treating agents in this invention are tri(alkylaryl)phosphites or a member of the group of the structural formula:

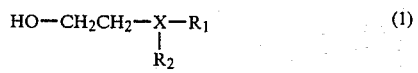

wherein $R_1$ and $R_2$ may be the same or different and represent hydrogen, an alkyl group of 1 to 10 carbon atoms, or $-CH_2CH_2OH$; and X is either nitrogen or phosphorous.

Hydrolysis of the complexed titanium residues is accomplished during steam distillation which is the conventional and accepted commercial method for removing excess alcohol from such reaction mixtures. Amounts of steam required for hydrolysis of complexed catalyst residues are normally less than amounts required for complete removal of alcohol. During the steam distillation, and as a result of the hydrolysis action of the contacting steam, the treated catalyst residues are converted to oxides of titanium and are thereupon rendered insoluble and precipitated from the reaction mixture in solid, crystalline form and may, thereafter, be conveniently filtered from the purified residue ester product. Products refined in the manner of this invention are high in purity, substantially free of residual titanium, low in acid number and generally suitable for applications requiring highest quality esters such as lubricants, and electrical, medical or food grade plasticizer applications.

DETAILED DESCRIPTION OF THE INVENTION

It is well known that organotitanates are active and desirable catalysts for synthesis of esters in reaction of carboxylic acids with alcohols. In the same way it is known that the commercial utility of such catalysts in ester manufacture is limited by the need to employ washing procedures to effect complete hydrolysis and removal of catalyst residues prior to distillation and final refining of the ester products. Such washing procedures are wasteful and costly, but attempts to avoid such washing normally results in only partial hydrolysis and incomplete removal of the titanium residues, accompanied by increase in acid numbers during steam distillation, difficult filtrations, and more color left in the product, lower thermal and storage stability and the like.

An object of this invention is to provide an improved method for removal of the titanium catalyst residues from the crude esterification mixture. An advantage of the invention is that it avoids caustic and water washing and, at the same time, provides products of equal or even better purity.

The basis of this invention rests in the discovery that certain compounds, which are chelating agents in the conventional sense, will act as scavengers in the reaction mixture, searching out and efficiently converting the titanium catalyst residues to substrates that are, by virtue of being complexed or otherwise associated with the chelating agent, rendered hydrolyzable and thereby easily removable by filtration from the purified ester.

In a preferred form of the invention, an esterification reaction mixture, in which the carboxylic acid has been converted to ester in the desired degree, normally not less than 99.95 percent, and which contains an excess of the reactant alcohol, along with titanium catalyst residues equivalent to 0.005 to 0.2 weight percent of the carboxylic acid charged to the reaction, is treated with a quantity of di-ethanolamine, or other chelating agent suitable to this invention, equivalent to 0.5 to 5.0 times the mole equivalent of titanium catalyst residues in the reaction mixture. This treatment is accomplished at a temperature below that at which the reaction was conducted and within the range of 25° C. to 200° C., and in a manner such that the chelating agent is thoroughly dispersed and in intimate contact with the entire reaction mixture for a suitable time, typically from one (1) to 60 minutes, prior to contacting with steam at reduced pressure, both for the purpose of removing excess alcohols and other volatile components and at the same time hydrolyzing the titanate catalyst residues. Typical conditions suitable to removal of alcohol and for hydrolysis of catalyst residues are quite broad, and may be accomplished in either batch or continuous methods. In a typical procedure, a quantity of ester, treated in the manner described above, is held at a temperature of between 100° C. and 200° C. while being contacted with a flow of steam at a pressure of 10 to 250 Torr for a time suitable to allow complete hydrolysis of the catalyst, as well as sufficient removal of excess alcohol and other volatile components. The amount of steam used and the time required vary with the apparatus, conditions of temperature and pressure, and the composition of the ester mixture. Typical and suitable conditions are illustrated in the examples of utility included herein.

Specific examples of suitable chelating agents for use in the present invention include tri-ethanolamine; N-alkyl-diethanolamines, such as N-methyl-diethanolamine, N-propyl-diethanolamine, N-butyl-diethanolamine and the like; N-N-dialkyl-ethanolamines, such as N,N-dimethyl-ethanolamine, N,N-diethyl-ethanolamine, N,N-dipropyl-ethanolamine, and the like; N-alkyl-ethanolamines, such as N-methyl-ethanolamine, N-ethyl-ethanolamine, N-propyl-ethanolamine, and the like. Analogous phosphite compounds can also be employed. Tri(alkylphenyl)phosphite compounds wherein the alkyl group contains 1 to 10 carbon atoms can also be employed as purification agents. The preferred purification agents for use in the present invention are di-ethanolamine and tri(isononylphenyl)phosphite.

It is believed that a necessary feature of the present invention is the presence of a trivalent nitrogen or phosphorous atom in the chelating agent, wherein an electron pair on the nitrogen or phosphorous atom remains free to function essentially as a Lewis base electron donor in the sense of the classical Lewis acid-base concept.

The advantages provided by this invention are several and diverse; improvements in yield, manufacturing costs and environmental considerations are available due to the simplicity offered by the process, while potential improvements in physical properties of acid number, filterability, color, storage stability, heat stability, electrical properties and overall purity are a result of the unique chemical application itself.

The improvement described by this invention brings the manufacture of esters to its simplist form (1) reaction, (2) stripping, and (3) filtration. While commercial processes have heretofore involved significant loss of time, raw materials and product due to neutralization of washing procedures, the method of this invention permits the use of titanate catalysts, which give the advantage of fast reaction rates, high conversion and efficient recycle of excess alcohols, without the need for neutralization and washing that are costly in time, yield and environmental requirements.

The examples below demonstrate the simplicity and the efficiency of the method, wherein the treating compounds are added to the residue following completion of the esterification reaction. This addition does not in fact cause additional steps or otherwise a delay in the refining process as the activity of the chelate treating compound with the titanium catalyst residues is fast and is versatile in temperature, being effective and efficient throughout the range from 25° C. to 200° C. While it is convenient to remove much of the excess alcohol with vacuum at the end of the esterification reaction and to add the chelate treating compounds at that time, while adjusting the temperature and conditions and apparatus for steam distillation, it is also effective to do the treatment before removing the alcohol.

Hydrolysis of the titanium catalyst residues, following treatment by the chelate compound, is easily and conveniently accomplished in a variety of conditions and methods, including simple agitation with a small amount of water, counter current washing, or with steam as is shown in examples herein. The steam treatment may be done in a batch situation, as shown here, or in counter current steam distillation systems as are commonly used for commercial manufacture of esters. Since steam distillation is the accepted, common and most efficient method for removal of alcohol, or other volatiles and odor to the very low levels required of esters for commercial use in plasticizers, lubricants, hydraulic, dielectric and other critical applications, it is convenient to use the same steam distillation procedure for both removal of low level volatiles and for hydrolysis of the treated titanium residues. The hydrolysis is quickly accomplished under the conditions of steam distillation, causing the formation of a fine precipitate of insoluble titanium oxides that are the products of the hydrolysis.

The efficiency with which the chelate treating compounds cause the titanium catalyst residues to be hydrolyzed and converted to insoluble, filterable solids is important to the quality of the resulting ester product. Thus, as is shown in the examples included herein, reaction mixtures treated in the manner of the invention do not increase in acid value during steam distillation, although significant increase is experienced during steam distillation of the same mixture that is not treated. In the same way the method of this invention provides important improvements in color, storage stability, heat stability, dielectric and other properties reflecting overall purity of the products.

EXAMPLE I

To a 2-liter flask was charged 222 g of phthalic anhydride and 468 g of 2-ethyl hexanol. The flask was fitted with a stir, thermometer, nitrogen purge line, Dean Stark type water separator and condenser. The system was purged with nitrogen, 0.5 g of tetraisopropyl titanate catalyst was added and the mixture heated to reflux. Water of reaction started to form at 165° C. The reaction temperature was allowed to rise to 205° C. and reflux maintained at 200° to 205° C. by adjusting the pressure. After 2.75 hours removal of water was complete and the acid value of the residue reduced to 0.03 mg KOH/g. At this time heating was terminated and excess alcohol removed by reducing the pressure to 30 Torr. The residue product, containing 1.5 percent excess alcohol, was adjusted to 175° C. and the remaining alcohol removed by steam distillation, this being accomplished by continuously introducing water in a dropwise fashion at a rate of about 1 ml/min. while maintaining conditions of 165° C. to 175° C. and 30 Torr. After 10 minutes of steam distillation a cloudiness indicating hydrolysis of the catalyst began to appear and continued to increase until the distillation was stopped after 30 minutes and 30 ml of water addition. The hydrolyzed residue product was dried for 5 minutes at 175° C. and 30 Torr, cooled at 90° C. and filtered with a No. 2 Buchner type filter and No. 1 Whatman paper coated with 3 g of diatomaceous earth filter aid. Filtration rate decreased rapidly and essentially stopped after 6 minutes. The clear filtrate had an acid number of 0.27 mg.KOH/g, color of 30 APHA and developed a cloudiness after 2 hours at room temperature.

EXAMPLE IA

An esterification reaction as described in Example I was carried out in the same manner, except that following removal of excess alcohol by vacuum distillation, and prior to steam distillation, 0.5 g of diethanolamine was added to the reaction mixture at a temperature of 175° C. and mixed intimately for a period of 15 minutes. Steam distillation was then conducted in the same manner as in Example I. Hydrolysis of the treated titanate catalyst residues was quite fast as a heavy white cloud of precipitate formed early in the steam distillation. Filtration was rapid, giving a clear product with 10 APHA color, 0.04 mg.KOH/g acid number and good storage stability.

EXAMPLE II

An esterification reaction as described in Example I is carried out in the same manner, except that following vacuum distillation, and prior to steam distillation, a 0.7 g portion of triethanolamine is added to the reaction mixture at a temperature of 175° C. and mixed intimately for a period of 15 minutes. At the end of that time the mixture is steam distilled as in Example I. The residue product exhibits a white suspension and in filtration continues to filter at a rapid rate until filtration is complete. The acidity of the filtrate is 0.04 mg.KOH/g which is essentially unchanged from the value before steam distillation refining. The filtrate remains clear even after extended storage.

EXAMPLE III

An esterification reaction as described in Example I is carried out in the same manner, except that following vacuum distillation, and prior to steam distillation, a 0.7 g portion of N-isopropyldiethanolamine is added to the reaction mixture at a temperature of 175° C. and mixed intimately for a period of 15 minutes. At the end of that time the mixture is steam distilled as in Example I. The residue product exhibits white suspension and in filtration continues to filter at a rapid rate until filtration is complete. The acidity of the filtrate is 0.03 mg.KOH/g which is essentially unchanged from the value before steam distillation refining. The filtrate remains clear even after extended storage.

EXAMPLE IV

An esterification reaction as described in Example I is carried out in the same manner, except that following vacuum distillation, and prior to steam distillation, 0.7 g portion of tri(isononylphenyl)phosphite is added to the reaction mixture at a temperature of 175° C. and mixed intimately for a period of 15 minutes. At the end of that time the mixture is steam distilled as in Example I. The residue product exhibits a white suspension and in filtration continues to filter at a rapid rate until filtration is complete. The acidity of the filtrate is 0.02 mg.KOH/g which is essentially unchanged from the value before steam distillation refining. The filtrate remains clear even after extended storage.

EXAMPLE V

To a 2-liter flask was charged 222 g phthalic anhydride, 800 g iso-tridecyl alcohol and 0.7 g tetra-decyl titanate catalyst. Reaction was conducted as in Example I, refluxing at 220° C. under reduced pressure until after 2.0 hours all water of reaction was collected and the acid number of 0.04 mg.KOH/g. Excess alcohol was removed by reducing pressure to 15 Torr. The crude ester, which contained 7.5 percent of alcohol was cooled and saved for refining:

(A) 270 parts of the crude product was mixed with 0.11 g of diethanolamine, heated to 170° C. and steam distilled at 100 Torr in the manner of Example I, using 43 ml of water during 60 minutes. After drying 10 minutes at 170° C. and 50 Torr, the product was filtered through No. 1 Whatman paper, collecting a very fine and red/brown precipitate. The filtrate was clear, having an acid number of 0.03 mg.KOH/g and color of 35 APHA. The filtrate (100 parts) was slurried with 0.1 part of activated carbon, heated to 110° C. for 5 minutes and filtered through a layer of diatomaceous earth to give a filtrate with color of 15 APHA.

(B) 270 parts of the crude product was heated to 170° C. and steam distilled at 100 Torr in the manner of Example I, using 60 ml of water in 60 minutes. After drying and filtration a precipitate was collected that was light tan and crystalline. The filtrate had an acid number of 0.08 and a color of 55 APHA. Treatment with activated carbon, as in A, gave a filtrate with color of 45 APHA.

EXAMPLE VI

To a one liter flask was charged 154 g trimellitic anhydride and 374 g of 2-ethylhexyl alcohol along with 0.3 g of tetra-butyl titanate catalyst. Reaction was conducted as in Example I, refluxing at 210° C. under reduced pressure until after 1.75 hours all water of reaction was removed and the acid number was 0.06 mg.KOH/g. After removing excess alcohol to 190° C. and 30 Torr, the temperature was adjusted to 150° C. and the crude reaction mixture, which contained 2.7 percent alcohol, was steam distilled as in Example I, using 30 ml of water during 30 minutes. After drying 5 minutes at 150° C. and 30 Torr, and filtration through a layer of diatomaceous earth, the product ester had a color of a 130 APHA and an acid number of 0.19 mg.KOH/g.

EXAMLE VII

The procedure of Example VI was repeated except that after vacuum distillation of excess alcohol and prior to steam distillation the crude product, which contained 2.5 percent alcohol, was adjusted to 150° C. and mixed with 0.3 g of diethanolamine. After 15 minutes the treated crude product was steam distilled using 30 ml of water during 30 minutes at 100 Torr. Rapid hydrolysis of the treated titanate catalyst residues was indicated by formation of the suspended precipitate. After drying and filtration through a layer of diatomaceous earth, the residue product had a color of 60 APHA and an acid number of 0.04 mg.KOH/g.

While the invention has been disclosed herein with certain embodiments, it is clear that modifications or equivalents can be used by those skilled in the art; accordingly, such changes within the principles of this invention are intended to be included within the scope of the claims below.

I claim:

1. In a process of preparing a refined liquid ester which comprises:
   (a) reacting one or more mono- or di-carboxylic acid or anhydride with an excess of alcohol in the presence of a catalytically effective amount of an organotitanate catalyst,
   (b) removing the water of esterification until esterification is essentially complete,
   (c) that improvement which comprises contacting the unrefined ester residue product with 0.01 to 4.0 weight percent of a treating agent selected from the group consisting of tri(alkylphenyl)phosphites, wherein said alkyl group contains one to ten carbon atoms, and a compound represented by the structural formula:

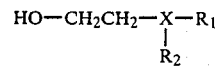

wherein X represents a nitrogen or a phosphorous atom and $R_1$ and $R_2$ are selected from the group consisting of hydrogen, $-CH_2CH_2OH$, and an alkyl group containing from 1 to 10 carbon atoms,
   (d) forming insolubles containing catalyst residues by steam distillation, and
   (e) filtering a purified ester product from the resulting hydrolyzed titanium catalyst residues.

2. The process as in claim 1 wherein the treating agent is di-ethanolamine.

3. The process as in claim 1 wherein the treating agent is ethanolamine.

4. The process as in claim 1 wherein the treating agent is tri-ethanolamine.

5. The process as in claim 1 wherein the treating agent is N-propyl diethanolamine.

6. The process as in claim 1 wherein the treating agent is tri(isononylphenyl)phosphite.

7. The process as in claim 1 wherein the treating agent is used in an amount of 0.1 to 2.0 weight percent per total weight of the acid reactants.

* * * * *